United States Patent [19]

Gebert et al.

[11] 4,213,994
[45] Jul. 22, 1980

[54] IMIDAZOLYL-(2)-CARBINOLS HAVING HYPOLIPIDEMIC ACTION AND PROCESS FOR PREPARING THEM

[75] Inventors: Ulrich Gebert; Ernold Granzer, both of Kelkheim, Fed. Rep. of Germany

[73] Assignee: Hoechst Aktiengesellschaft, Frankfurt, Fed. Rep. of Germany

[21] Appl. No.: 6,203

[22] Filed: Jan. 24, 1979

Related U.S. Application Data

[63] Continuation of Ser. No. 351,523, Apr. 16, 1973, abandoned, which is a continuation-in-part of Ser. No. 318,110, Dec. 26, 1972, abandoned.

[30] Foreign Application Priority Data

Dec. 28, 1971 [DE] Fed. Rep. of Germany ....... 2164919

[51] Int. Cl.$^2$ .................. A61K 31/415; C07D 233/64; C07D 235/12
[52] U.S. Cl. ........................... 424/273 R; 424/273 B; 548/327; 548/330; 548/331; 548/336; 548/342; 548/343; 548/345
[58] Field of Search ............... 548/342, 336, 330, 327, 548/345; 424/273 R, 273 B

[56] References Cited

U.S. PATENT DOCUMENTS

| | | | |
|---|---|---|---|
| 3,652,579 | 3/1972 | Hoffer et al. | 548/342 |
| 3,812,189 | 5/1974 | Pollard et al. | 548/342 |

FOREIGN PATENT DOCUMENTS 2164919  7/1973  Fed. Rep. of Germany ........... 548/342

OTHER PUBLICATIONS

Behringer et al., Chem. Ber. 1966, vol. 99, pp. 1815-1821.
Rohr et al., Chem. Ber. 1968, vol. 101, pp. 3491-3498.
Roe J. Chem. Soc. (London) 1963, pp. 2195-2200.
Shirley et al., J. Amer. Chem. Soc. 1957, vol. 79, pp. 4922-4927.
Tertov et al., Chem. Abst. 1971, vol. 74, No. 76466e.
Lawesson et al., Tetrahedron 1968, vol. 24, pp. 1875-1888.
O'Sullivan et al., I Chem. Abst. 1964, vol. 60, col. 10669.
O'Sullivan et al., II Experienta 1971, vol. 27, pp. 1025-1027.
Otaki et al., J. Pharm. Soc. Japan 1965, vol. 85, pp. 926-935.
Sinnur et al., Chem. Abst. 1966, vol. 65, col. 12192.
Zellner et al., Monatsh. Chem. 1967, vol. 98, pp. 643-665.

*Primary Examiner*—Natalie Trousof
*Attorney, Agent, or Firm*—Curtis, Morris & Safford

[57] ABSTRACT

Pharmaceutical preparations having hypolipidemic activity, which contain in addition to a pharmaceutically acceptable carrier an effective amount of an imidazolyl-(2)-carbinol of the general formula I in which R represents hydrogen, lower alkyl, phenyl or benzyl, $R_1$ and $R_2$ each represent hydrogen or together the group —CH=CH—CH=CH—, $R_3$ and $R_4$ represent hydrogen, lower alkyl, phenyl, lower haloalkyl, lower alkylphenyl, lower alkoxyphenyl, lower haloalkoxyphenyl, mono- or dihalophenyl, imidazolyl or benzylimidazolyl or $R_3$ and $R_4$ are together fluoryl of the formula or of a physiologically tolerable acid addition salt thereof, and process for preparing them.

25 Claims, No Drawings

IMIDAZOLYL-(2)-CARBINOLS HAVING HYPOLIPIDEMIC ACTION AND PROCESS FOR PREPARING THEM

This is a Continuation in Part Application of our copending U.S. Pat. application Ser. No. 351,523 filed on Apr. 16, 1973 by Ulrich Gebert et al., now abandoned, which is a Continuation in Part Application of U.S. Pat. application Ser. No. 318,110 filed on Dec. 26, 1972 by U. Gebert et al., now abandoned.

It is known that basic 1,1,2-triphenyl-ethanols of the type

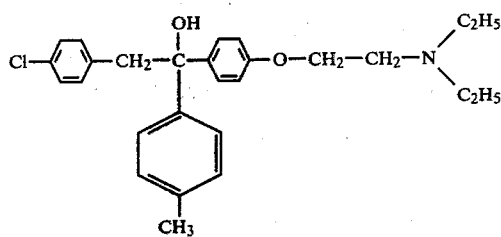

have hypocholesterinemic activity (Fortschr. Arzneimittelforschung 13, 235 (1969)) and that their p-diethyl-aminoethoxyphenyl group can be exchanged without loss of activity against the pyridine ring (J. Med. Chem. 7, 113 (1964)). Also triarylmethanols and their derivatives in which a benzene ring has been replaced by the pyridyl group (J. Med. Chem. 8, 223 (1965)), or by a thienyl or furyl group (U.S. Pat. No. 3,097,206) have been described to be cholesterin-lowering agents.

Now, we have found that imidazolyl-(2)-carbinols of the general formula

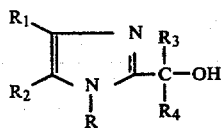

in which
R represents a hydrogen atom, lower alkyl, phenyl or benzyl,
$R_1$ and $R_2$ each represent a hydrogen atom or together the group —CH═CH—CH═CH—,
$R_3$ and $R_4$ represent hydrogen, lower alkyl, phenyl, lower haloalkyl, lower alkyl-phenyl, lower alkoxyphenyl, lower haloalkoxyphenyl, mono- or di-halophenyl, imidazolyl or benzylimidazolyl or
$R_3$ and $R_4$ together fluoryl of the formula

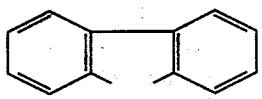

and their non-toxic acid addition salts not only have hypocholesterinemic action, but are partly also able to provoke a long-lasting lowering of the triglyceride level in the blood serum.

In the preceding and following definitions, the terms "lower alkyl" and "lower alkoxy" always stand for such a group which contains 1 to 4 carbon atoms in a straight or branched chain.

Accordingly, the object of the invention are hypolipidemically active imidazolyl-(2)-carbinols of the formula I and process for preparing them.

Thus, the imidazolyl-(2)-carbinols of the formula I can be prepared by a process, wherein
(a) imidazoles of the formula

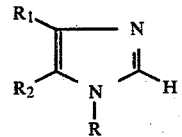

which are metallized in 2-position, are reacted with carbonyl compounds of the formula $R_3$—CO—$R_4$ (III) and the alcoholates obtained are hydrolized,
(b) imidazoles of the formula II

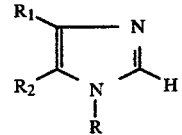

which are metallized in 2-position are reacted with esters of the formula IV

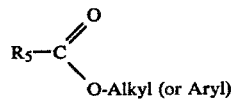

in which $R_5$ has the meanings given for $R_3$ and $R_4$, respectively, above, with the exception of imidazolyl, benzylimidazolyl and fluoryl, at a molar ratio of 2:1, and the alcoholates obtained are hydrolyzed,
(c) 2-acylimidazoles of the formula V

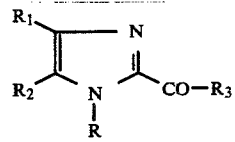

in which R, $R_1$, $R_2$ and $R_3$ have the meanings given above, are reacted with Grignard compounds of the formula VI

in which $R_4$ has the meaning given above, with the exception of hydrogen, imidazolyl and benzylimidazolyl, and Hal stands for a chlorine, bromine, or iodine atom, and the intermediate products are hydrolyzed, and the reaction products are debenzylated if necessary (if R=benzyl) and, if desired, converted into non-toxic acid addition salts by treatment with acids.

Preferably, the substituent R represents a straight chain or branched alkyl group of 1 to 3 carbon atoms, such as methyl or isopropyl, or the phenyl or benzyl group.

Such compounds, wherein $R_3$ and $R_4$ are different, are preferred. As radicals $R_3$ and $R_4$, there may thus be used: hydrogen, —$CH_3$, —$C_2H_5$, —$C_3H_7$, —$C_4H_9$, —$CCl_3$, —$CHCl_2$, —$CH_2CCl_3$, —$CF_2Cl$, —$CBr_3$, $CF_3$, phenyl which may be substituted by F, Cl, Br, $CHF_2CF_2O$—, $CHFClCF_2$—O—, $CHCl_2CF_2$—O—, —$CH_3$, $C_2H_5$—.

The preferred compounds can be defined by the general formula I(a)

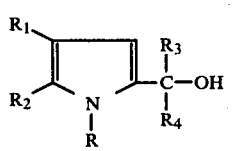

wherein
R = lower alkyl, phenyl or benzyl,
$R_1$ and $R_2$ = hydrogen or together —CH=CH—CH=CH—,
$R_3$ = hydrogen, lower alkyl or phenyl,
$R_4$ = lower haloalkyl, lower haloalkoxyphenyl, benzylimidazolyl, monohalophenyl, dihalophenyl or $R_3$ and $R_4$ are together fluoryl of the formula

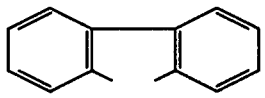

all of said alkyl and alkoxy groups having 1 to 4 carbon atoms, and their physiologically tolerable acid addition salts.

The imidazolyl-(2)-carbinols are prepared according to method (a), for example by reacting corresponding imidazoles or benzimidazoles substituted in the 1-position and corresponding to the general formula II

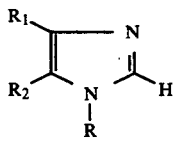

with aryl- or alkyl-lithium, preferably butyl-lithium, in anhydrous diethyl ether to obtain derivatives metallized in the 2-position, which are then added to carbonyl compounds of the general formula III $R_3$—CO—$R_4$   III This operation is carried out advantageously under an atmosphere of nitrogen. While the addition of the heterocyclic Li-compounds on aldehydes of the formula III is generally carried out at −50° C., the reaction with the ketones of the formula III requires reaction temperatures in the range of between 0° and 30° C.

Tertiary bis-[1-alkyl (or aryl)-imidazolyl-(2)]-carbinols of the general formula

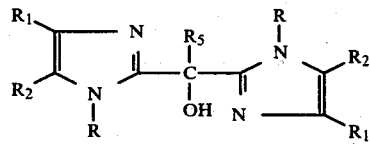

in which $R_5$ has the meanings given for $R_3$ or $R_4$ with the exception of hydrogen, imidazolyl, benzylimidazolyl and fluoryl, can be prepared, besides accordings to method (a), also according to method (b), by metallizing compounds of the formula II with butyllithium and reacting with carboxylic acid alkyl (or aryl) esters of the general formula IV

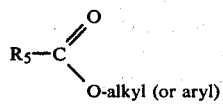

at a molar ratio of 2:1.

The lithium alcoholates formed primarily are then decomposed hydrolytically after completed reaction.

The reaction according to method (c) is likewise most suitably carried in single batch reaction, by preparing in known manner the Grignard compounds of the formula VI and adding dropwise, while cooling, a solution of the 2-acylimidazole of the formula V preferably in an ether. The reaction mixture is then boiled, preferably for 1.5 to 3 hours, under reflux.

The compounds which are not substituted at the nitrogen atom in the imidazole part can be prepared from corresponding N-benzyl-derivatives by hydrogenolytic debenzylation with sodium in liquid ammonia or with catalytically excited hydrogen.

Conversion of the free bases into non-toxic acid addition salts for example hydrochlorides, tosylates and mesylates, is effected in known manner.

The preparation of the starting compounds of the formula II used according to methods (a) and (b) has been described several times in literature (cf. for example, D. A. Shirley et al., Chem. Soc. 79 (1957), page 4922; A. M. Roe, J. Chem. Soc. (London) 1963, page 2195). The 2-acylimidazoles of the formula V which are used according to method (c) as one of the two starting compounds are prepared according to the indications given in DOS 1,926,206 and DOS 1,956,711.

Since it is today generally believed that increased serum lipid values are important hazard factors in the genesis of arteriosclerotic diseases, and that not only in the field of the coronary vessels, the interest in chemical compounds having hypolipidemic activity is steadily increasing.

While having an extremely low acute toxicity (cf. $LD_{50}$-values in Table I), the imidazolyl-(2)-carbinols reduce the lipid level in the serum and reduce artificially produced hyperlipidemia. This was demonstrated on animal experiments wherein Clofibrate (2-(p-chlorophenoxy)-isobutyric acid ethyl ester) was used as comparative substance.

1. Standard test on a male rat with normal serum lipid level

The period of time used for the experiment was 8 days. Administration was effected once daily with the aid of an oesophageal sound with doses of 100, 30 and 10 mg/kg, respectively. In general, blood was withdrawn prior to and after the treatment and the concentration of cholesterin was determined in the serum according to the method described by Lauber and Richterich and that of triglycerides according to the method described by Eggstein and Kreutz. The values calculated from these data for the reduction of the serum lipid level are compiled in Table I.

Table I

Hypolipidemic Action
% change in the standard test after 8 peroral administrations of mg/kg/day

| Compound from Example ($LD_{50}$ in g/kg) | 100 Serum-Cholesterin | Serum-triglycerides | 30 Serum-Cholesterin | Serum-triglycerides | 10 Serum-Cholesterin | Serum-triglycerides |
|---|---|---|---|---|---|---|
| 1 (>4) | | | −33/−10 | −25/−10 | −10/−12 | /−13 |
| 2 (1.123) | −24/−3 | /−4 | | | | |
| 3 (>4) | −6/−18 | −57/−30 | −16/ | −21/−6 | | |
| 4 (>4) | −16/−21 | −48/−37 | −11/ | −25/ | | |
| 5 (>4) | −19/−32 | −37/−35 | −23/−9 | −1/−17 | | |
| 6 (>4) | −12/−25 | −46/−35 | −20/ | −19/−29 | | |
| 7 (>4) | −7/ | −18/−18 | | | | |
| 8 (>4) | −14/ | −39/−21 | | | | |
| 9 (>4) | −21/−11 | −40/−24 | | | | |
| 10 (>4) | −36/−21 | −56/−26 | | | | |
| 11 (>4) | −24/−3 | −32/−21 | | | | |
| Clofibrate(2-2.5) | −22/−13 | −30/−30 | −5/−8 | −4/−7 | ineffective | ineffective |

The values in brackets of the first column designate the $LD_{50}$-values in g/kg, determined on the mouse upon oral administration. The values before the oblique stroke of the other columns denote the percentual change of the posterior value (value after the treatment) referred to the anterior value (starting value before the treatment) of the group of preparations, the anterior value being 100%; the values behind the oblique stroke indicate the percentual change of the posterior value of the group treated with reference to the posterior value (= 100%) of a placebo group.

2. Triton-Hyperlipidemia of the male rat

The influence of a 4-days pre-treatment with the compound of Example 1 on the formation of hyperlipidemia produced by i.p. application of 300 mg/kg of Triton ®WR 1339 was tested in comparison to a control group (=100%) which had only been treated with Triton.

Table II

| | Inhibition of triton-hyperlipidemia | | | |
|---|---|---|---|---|
| | 100 mg/kg/day p.o. | | 10 mg/kg/day p.o. | |
| Preparation | Serum-cholesterin | Serum-triglyceride | Serum-cholesterin | Serum-triglyceride |
| from Example 1 | −28% | −35% | −31% | −40% |
| Clofibrate | −29% | −16% | ineffective | ineffective |

3. Dietetic hypercholesterinemia of the male rat

Hypercholesterinemia was produced by the addition of 2% of of cholesterin and 20% of coconut fat (Palmin) to the normal fodder. The rise of the cholesterin level was determined by comparison with a control group (=100%) which had been given normal fodder only. (Line 1 in Table III). The animals of the preparation group obtained at the same time of the begin of the diet daily once 100 mg/kg p.o. of the compound of Example 1. After 8, 20 and 23 days, the average concentration of the total cholesterin in the serum was determined and compared with that of the control group (=100%) which had been fed with the diet (line 2 in Table III).

Table III

| | Inhibition of dietetic hypercholesterinemia | | |
|---|---|---|---|
| | % change of the total cholesterin content in the serum after days | | |
| Effect | 8 | 20 | 33 |
| Increase due to the diet (normal food = 100%) | +37 | +2 | +51 |
| Inhibition due to preparation (diet = 100%) | −23 | −19 | −9 |

The compounds of the formula I are distinctly superior, in particular at smaller doses, to Clofibrate. A number of imidazolyl-(2)-carbinols of the general formula I, e.g. the compound of Example 2, is known and described by D. A. Shirley et al. (Chem. Soc. 79 (1957), p. 4922-4927) and A. M. Roe (J.Chem.Soc. (London) 1963 p. 2195-2200). But it is not known from the prior art that the compounds of the formula I possess hypolipidemic activity.

Owing to their hypolipidemic activity, the compounds of the formula I may be used as hypolipidemic agents in the treatment of hyperlipidemias. The dose to be administered daily is in the range of from 0.25 g to 4 g, preferably between 0.75 and 2 g; preferably, it is administered orally, 2 to 4 times per diem, in several partial amounts of between 100 and 1000 mg, preferably between 250 and 500 mg. The compounds may be administered orally either alone or in admixture with other active substances or excipients or adjuvants, in the form of tablets, dispersible powders, granules, capsules, elixirs, suspensions or syrups. The respective preparations can be prepared according to known methods. They may contain the usual additives such as sweetening agents, aromatics dyestuffs or conserving agents. The tablets may contain the active substance in admixture with the pharmaceutically usual excipients and adjuvants, for example inert diluents such as lactose, talc, calcium carbonate, auxiliary agents for granulation and comminution, for example starch, alginic acid, or binders such as starch, gelatin, and sliding agents such as stearic acid, magnesium stearate or talc. They may be provided with a coating which delays decomposition and absorption in the gastrointestinal tractus and thereby provoke a long-lasting action. In similar manner, the suspensions, syrups or elixirs may contain the active substance together with the usual auxiliary agents. As suspending agents there may be used, for example methyl-cellulose, tragacanth or sodium alginate. As wetting agents, there may be used for this purpose lecithin, sorbitane-monooleate, polyoxyethylene stearate, and as conserving agent, for example parahydroxymethylbenzoate. For the preparation of capsules, there may be used, as diluents, for example calcium phosphate, caolin or calcium carbonate. Pharmaceutical preparations which are preferred from the point of view of preparation and simple and easy administration are solid preparations, in particular hard-filled capsules or tablets which contain the active substance in an amount of 250 or 500 mg.

A particular use of the products of the formula I comprises their combination with other active substances. These are, in addition to other appropriate substances, above all cardiac and blood circulation agent and antidiabetics.

The following Examples illustrate the invention. The structure of the described compounds was determined from elementary analysis, infrared- and NMR-spectroscopie data.

EXAMPLE 1

Bis-[1-benzylimidazolyl-(2)]-phenyl-carbinole (a) An ethereal solution of 0.4 moles of butyl-lithium (prepared cf. Org. Reactions 6, 352 (1951)) was added dropwise while stirring, at $-45°$ to $-50°$ C., to 63.3 g (0.4 mole) of 1-benzylimidazole in 1000 ml of anhydrous ether, the whole was then stirred for 1 hour and a solution of 30 g (0.2 mole) of benzoic acid ethyl ester in 100 ml of ether was added dropwise. The reaction mixture was allowed to warm up to room temperature and then heated for 2 hours under reflux, the product was extracted with 2 N-hydrochloric acid, the acid extract was rendered alkaline with 2 N-sodium hydroxide solution and extracted with chloroform. After drying over sodium sulfate and removal of the solvent under reduced pressure, the solid residue was recrystallized from methanol. Yield: 68 g (81% of the theory); melting point 162°–163° C.

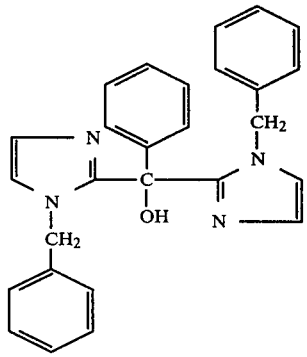

$C_{27}H_{24}N_4O$ MW 420.5
Analysis
Calc.: C 77.2%; H 5.7%; N 13.3%; Found: C 77.4%; H 5.7%; N 13.4%.

(b) 40 g of bromobenzene in 100 ml of anhydrous ether were added to 6.4 g of magnesium chips, while stirring and after having added some iodine crystals. Dosage was effected in such a manner that the reaction under moderate reflux continuously proceeded automatically. Boiling was then continued for 1 hour, during which time the metal dissolved almost completely. 68.4 g (0.2 mole) of bis-[1-benzylimidazolyl-(2)]-ketone in 500 ml of anhydrous tetrahydrofurane was added, while cooling with ice, from a dropping funnel. The reaction mixture was boiled for 2 hours on a reflux cooler, worked up as described under 1(a). 80 g of crude product were obtained and the crude product was recrystallized from the methanol.

Yield: 65 g (77% of the theory); melting point 161°–162° C.
Analysis:

Calc.: C 77.2%; H 5.7%; N 13.3%; Found: C 77.4%; H 5.8%; N 13.3%.

Bis-[1-benzylimidazolyl-(2)]-ketone

The ketone used as starting material in Example 1(b) was obtained by the reaction of 1-benzylimidazolyl-(2)-lithium with carbonic acid diethyl ester in a molar ratio of 2:1 in ether as solvent, by allowing the reaction mixture to react for 5 hours at $-40°$ C. and for 2 hours at room temperature. Isolation was carried out as described under 1(a) by acid-base extraction and redissolution from ethyl acetate.

Yield: 88% of the theory; melting point 135°–137° C.

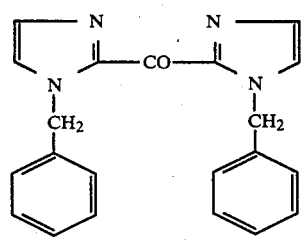

$C_{21}H_{18}N_4O$ MW 342.4
Analysis:
Calc.: C 73.7%; H 5.3%; N 16.35%; Found: C 73.7%; H 5.3%; N 16.3%.

EXAMPLE 2

1-[1-benzylimidazolyl-(2)]-ethanol 63.3 g (0.4 mole) of 1-benzylimidazole were dissolved in 400 ml of ether and metallized as described in Example 1. Then, 26.4 g (0.6 mole) of acetaldehyde were added in one portion, whereupon the temperature rose to about $-30°$ C., the whole was stirred for 1 hour at $-50°$ C. and the temperature of the reaction mixture was allowed to rise to room temperature and the product was freed from non-basic components by the acid-base extraction described in Example 1. The solid residue from the chloroform extract was recrystallized from ethyl acetate.

Yield: 71 g (88% of the theory); melting point 106°–107° C.

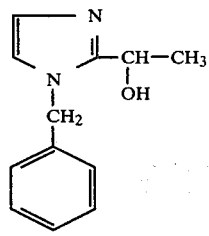

$C_{12}H_{14}N_2O$ MW 202.2
Analysis:
Calc.: C 71.25%; H 7.0%; N 13.85%; Found: C 71.2%; H 6.9%; N 14.0%.

EXAMPLE 3

1-[1-Isopropylimidazolyl-(2)]-2,2,2-trichloroethanol 11.0 g (0.1 mole) of isopropylimidazole were metallized in 200 ml of ether at $-50°$ C. as described in Example 1 and combined with 17.8 g (0.1 mole) of anhydrous chloral in 30 ml of ehter and stirred overnight in the cold. Working was effected as described in Example 1 by acid-base extraction. The chloroform phase left a solid substance upon evaporation under reduced pressure; the substance could be recrystallized from ethyl acetate.

Yield: 15 g (58% of the theory); melting point 186°–187° C.

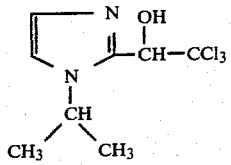

$C_8H_{11}Cl_3N_2O$ MW 257.6
Analysis:
Calc.: C 37.3%; H 4.3%; Cl 41.3%; N 10.9%; Found: C 37.4%; H 4.6%; Cl 41.5%; N 10.6%.

EXAMPLE 4

9-[1-Benzylimidazolyl-(2)]-fluorene-9-ol

A solution of 21.6 g (0.12 mole) of fluorenone in 150 ml of ether was added to 0.1 mole of 1-benzylimidazolyl-(2)-lithium (prepared as described in Example 1). When the reaction mixture had come to room temperature, it was stirred for 5 hours, the alcoholate was decomposed by the addition of water and the solid product that had precipitated was filtered off with suction, washed with water until it was neutral and recrystallized from a mixture of ethanol and water. The yield could slightly be increased by extraction of the two-phase filtrate with chloroform.

Yield: 16.7 (50% of the theory); melting point 147°–148° C.

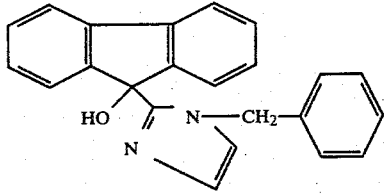

$C_{23}H_{18}N_2O$ MW 338.4
Analysis:
Calc.: C 81.6%; H 5.4%; N 8.3%; Found: C 81.3%; H 5.3%; N 8.3%.

EXAMPLE 5

Phenyl-(2,4-dichlorophenyl)-[1-methylimidazolyl-(2)]-carbinol 8.2 g (0.1 mole) of 1-methylimidazole were dissolved in 200 ml of anhydrous ether and metallized at −30° C. as described in Example 1. Then, 25, 1 g (0.1 mole) of 2,4-dichlorobenzophenone werde added, the whole was stirred for 5 hours at room temperature, decomposed with water, the solid substance that had precipitated was filtered off with suction, the filtrate which had an alkaline reaction was extracted with chloroform, the residue obtained upon evaporation of this extract was combined with the material that had been filtered off with suction and the whole was eventually recrystallized from a mixture of ethanol and water.

Yield: 24.5 (74% of the theory); melting point 181°–182° C.

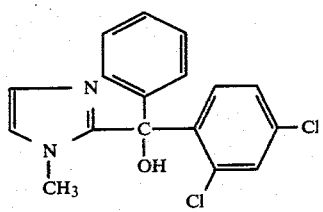

$C_{17}H_{14}Cl_2N_2O$ Mw 333.2
Analysis:
Calc.: C 61.3%; H 4.2%; Cl 21.3%; N 8.4%; Found: C 61.2%; H 4.2%; Cl 21.1%; N 8.5%.

EXAMPLE 6

Phenyl-(2,4-dichlorophenyl)-[1-methylbenzimidazolyl-(2)]-carbinol 13.2 g (0.1 mole) of 1-methylbenzimidazole were reacted as described in Example 5. However, in order to avoid side reactions, the metallization had to be carried out at very deep temperatures (below −60° C.). Since the base upon decomposition of the alcoholate with water did not separate in the form of a solid product, it was extracted with chloroform and then recrystallized from a mixture of ethanol and water.

Yield: 24.3 g (63% of the theory); melting point 154°–156° C.

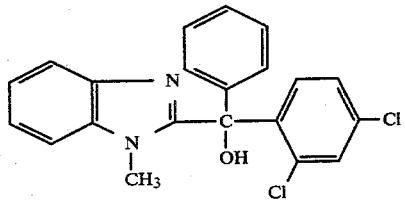

$C_{21}H_{16}Cl_2N_2O$ MW 383.3
Analysis:
Calc.: C 65.8%; H 4.2%; Cl 18.5%; N 7.3%; Found: C 66.0%; H 4.3%; Cl 18.6%; N 7.0%.

EXAMPLE 7

Bis-[imidazolyl-(2)]-phenyl-carbinol

About 5.8 g (0.25 gram-atoms) of sodium in the form of small pieces were introduced slowly, at −40° C., into a solution of 21.0 g (0.05 mole) of bis-[1-benzylimidazolyl-(2)]-phenyl-carbinol (cf. Example 1) in 350 ml of liquid ammonia and 70 ml of anhydrous ether, until the blue coloration remained constant, the whole was then stirred for 30 minutes, then discoloured with the required quantity of ammonium chloride, 13.4 g (0.25 mole) of ammonium chloride were added and the ammonia was evaporated. The residue was dissolved in 4 N-hydrochloric acid and for removing the toluene and dibenzyl that had formed, it was extracted with ether. Upon addition of solid potash until the reaction was alkaline, the compound precipitated. Since it was not soluble or poorly soluble only in the usual solvents, it was purified by dissolution and precipitation from a hydrochloric solution with sodium hydroxide solution.

Yield: 11.6 g (96% of the theory); melting point 240°–242° C. (decomposition).

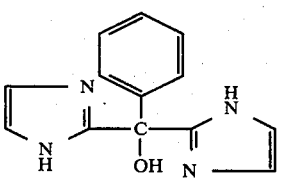

C$_{13}$H$_{12}$N$_4$O MW 240.3
Analysis:
Calc.: C 65.0%; H 5.0%; N 23.3%; Found: C 64.6%; H 5.0%; N 23.5%.

EXAMPLE 8

Methyl-(p-chlorophenyl)-[1-isopropylimidazolyl-(2)]-carbinol 0.1 mole of 1-isopropylimidazolyl-(2)-lithium (cf. Example 3) in 200 ml of ether yielded upon reaction with 15.9 g (0.1 mole) of 4-chloroacetophenone (dissolved in 30 ml of ether) within 3 hours at room temperature, working up according to Example 6 and crystallization from ethyl acetate, 18.5 g (70% of the theory); melting point 201°–203° C.

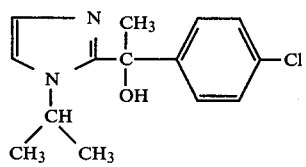

C$_{14}$H$_{17}$ClN$_2$O MW 264.8
Analysis:
Calc.: C 63.5%; H 6.5%; Cl 13.4%; N 10.6%; Found: C 63.6%; H 6.4%; Cl 13.5%; N 10.7%.

EXAMPLE 9

[1-Benzylimidazolyl-(2)]-[1-methylbenzimidazolyl-(2)]-carbinol 18.6 g (0.1 mole) of 1-benzyl-2-formylimidazole (Liebigs Ann. Chem. 718, 249 (1968)) in 30 ml of ether were added dropwise to a solution of metallized 1-methylbenzimidazole (13.2 g=0.1 mole) in anhydrous ether (cf. Example 6), at −55° C. and then stirred for 2 hours at −50° C. and further 2 hours at room temperature. Isolation was carried out according to the acid-base extraction and redissolution in ethyl acetate.

Yield: 18.7 g (59% of the theory); melting point 167°–169° C.

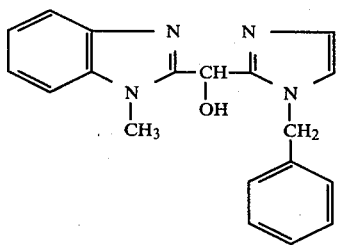

C$_{19}$H$_{18}$N$_4$O MW 318.4
Anaylsis:
Calc.: C 71.7%; H 5.7%; N 17.6%; Found: C 71.6%; H 5.6%; N 17.7%.

EXAMPLE 10

1-[p-(1,1,2-trifluoro-2-chloro-ethoxy)-phenyl]-1-[1-benzylimidazolyl-(2)]-ethanol 25.3 g (0.1 mole) of p(1,1,2-trifluoro-2-chloroethoxy)acetophenone (Bull. Soc. Chim. France 1962, 254), mixed with 30 ml of ether were added at −50° C., to 0.1 mole of 1-benzylimidazolyl-(2)-lithium in 200 ml of anhydrous ether (cf. Example 1), the whole was stirred for 3.5 hours at room temperature the lithium alcoholate was decomposed with water and the product was extracted with chloroform. Recrystallization was effected with a mixture of ethanol and water.

Yield: 23.8 g (58% of the theory); melting point 155°–157° C.

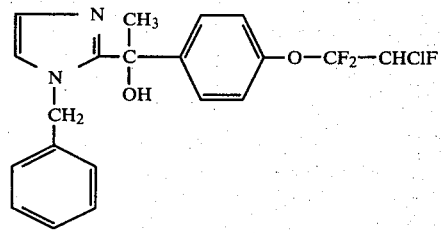

C$_{20}$H$_{18}$ClF$_3$N$_2$O$_2$ MW 410.8
Analysis:
Calc.: C 58.5%; H 4.4%; Cl 8.6%; F 13.9%; N 6.8%; Found: C 58.2%; H 4.5%; Cl 8.9%; F 13.8%; N 6.5%.

EXAMPLE 11

(3,4-Dimethoxy-phenyl)-[1-phenylimidazolyl-(2)]-carbinol 14.4 g (0.1 mole) of 1-phenylimidazole in 100 ml of ether were metallized as described in Example 1 with butyl-lithium at −50° C. and then reacted with 16.6 g (0.1 mole) of 3,4-dimethoxybenzaldehyde dissolved in 80 ml of ether. The whole was stirred for 1 hour at −50° C. and then for 2 hours at room temperature. Working up was carried out by acid-base extraction (as described in Example 1). After crystallization from ethyl acetate, there were obtained 26.9 g (87% of the theory); melting point 137°–138° C.

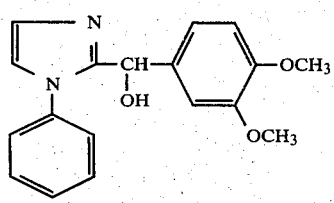

3

C$_{18}$H$_{18}$N$_2$O$_3$ MW 310.4
Analysis:
Calc.: C 69.7%; H 5.8%; N 9.0%; Found: C 69.6%; H 5.7%; N 8.7%.

EXAMPLE 12

Tablets were prepared from the following components: 150 mg of one of the compounds described in Examples 1-11 in ground state, 140 mg of maize starch, 45 mg of pulverized lactose, 30 mg of talc, 30 mg of amylopectin and 5 mg of magnesium stearate.

EXAMPLE 13

500 mg of one of the compounds described in Examples 1 to 11 were filled in ground state into special gelatine capsules of Messrs. Scherer.

EXAMPLE 14

Liquid suspension for oral administration: 5 g of one of the compounds described in Examples 1 to 11 in ground state, 65 g of starch syrup, 5 g kaolin Supreme, 5 mg of sodium saccharin, 2 ml of orange sweet essence, 0.03 g of parahydroxybenzoic acid methyl ester, 100 ml of demineralized water; 1 tea spoon (5 g) of the syrup obtained in this manner contained 250 mg of active substance.

EXAMPLE 15

Tablets having a content of active substance of 500 mg were prepared from the following components: 500 mg of one of the active compounds described in Examples 1 to 11, 140 mg of lactose, 160 mg of maize starch, 30 mg of methylcellulose, 25 mg of talc, 5 mg of magnesium stearate. The active substances were mixed with lactose and maize starch and granulated with a 10% maize starch paste. The granules so produced were sieved through a sieve having a mesh size of 0.8 mm and then methylcellulose, talc and magnesium stearate were admixed to the granules. The mixture was homogenized and compressed to tablets.

We claim:

1. An imidazolyl-2-carbinol of the formula I(a)

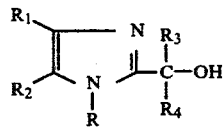

wherein
R = lower alkyl, phenyl or benzyl,
$R_1$ and $R_2$ = hydrogen,
$R_3$ = hydrogen, lower alkyl or phenyl,
$R_4$ = lower haloalkyl, lower haloalkoxyphenyl, 1-benzylimidazol-2-yl, monohalophenyl, dihalophenyl or $R_3$ and $R_4$ are together fluoryl of the formula

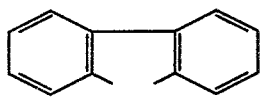

all of said alkyl and alkoxy groups having 1 to 4 carbon atoms, and the physiologically tolerable acid addition salts.

2. An imidazolyl-2-carbinol of the formula

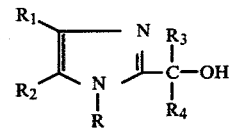

wherein
R is lower alkyl of one to four carbons, phenyl or benzyl,
$R_1$ and $R_2$ are hydrogen,
$R_3$ is lower alkyl or phenyl,
$R_4$ is monohalophenyl or dihalophenyl.

3. An imidazolyl-2-carbinol of the formula

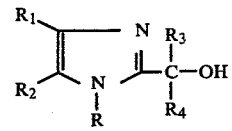

wherein
R is lower alkyl of one to four carbons, phenyl or benzyl,
$R_1$ and $R_2$ are hydrogen,
$R_3$ is phenyl and
$R_4$ is dihalophenyl.

4. Bis-[1-benzylimidazolyl-(2)]-phenyl-carbinol.
5. 1-[1-Isopropylimidazolyl-(2)]-2,2,2-trichloroethanol.
6. 9-[1-Benzylimidazolyl-(2)]-fluorene-9-ol.
7. Phenyl-(2,4-dichlorophenyl)-[1-methylimidazolyl-(2)]-carbinol.
8. Phenyl-(2,4-dichlorophenyl)-[1-methylbenzimidazolyl-(2)]-carbinol.
9. Methyl-(p-chlorophenyl)-[1-isopropylimidazolyl-(2)]-carbinol.
10. [1-Benzylimidazolyl-(2)]-[1-methylbenzimidazolyl-(2)]-carbinol.
11. 1-[p-(1,1,2-Trifluoro-2-chloroethoxy)-phenyl]-1-[1-benzylimidazolyl-(2)]-ethanol.
12. A pharmaceutical composition useful in lowering the serum lipid level in the treatment of hyperlipidemia consisting essentially of a pharmaceutically acceptable carrier and from 100 to 1000 mg per dosage unit of a compound of the formula I(a)

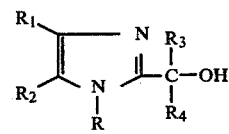

wherein
R = lower alkyl, phenyl or benzyl,
$R_1$ and $R_2$ = hydrogen,
$R_3$ = hydrogen, lower alkyl or phenyl,
$R_4$ = lower haloalkyl, lower haloalkoxyphenyl, 1-benzylimidazol-2-yl, monohalophenyl, dihalophenyl or $R_3$ and $R_4$ are together fluoryl of the formula

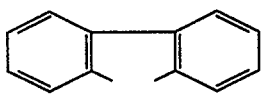

all of said alkyl and alkoxy groups having 1 to 4 carbon atoms, or of a physiologically tolerable acid addition salt thereof.

13. A pharmaceutical preparation as claimed in claim 12, wherein the imidazolyl-(2)-carbinol is bis-[1-benzylimidazolyl-(2)]-phenyl-carbinol.

14. A pharmaceutical preparation as claimed in claim 12, wherein the imidazolyl-(2)-carbinol is 1-[1-isopropylimidazolyl-(2)]-2,2,2-trichloroethanol.

15. A pharmaceutical preparation as claimed in claim 12, wherein the imidazolyl-(2)-carbinol is 9-[1-benzylimidazolyl-(2)[-fluorene-9-ol.

16. A pharmaceutical preparation as claimed in claim 12, wherein the imidazolyl-(2)-carbinol is phenyl-(2,4-dichlorophenyl)-[1-methylimidazolyl-(2)]-carbinol.

17. A pharmaceutical preparation as claimed in claim 12, wherein the imidazolyl-(2)-carbinol is phenyl-(2,4-dichlorophenyl)-[1-methylbenzimidazolyl-(2)]-carbinol.

18. A pharmaceutical preparation as claimed in claim 12, wherein the imidazolyl-(2)-carbinol is methyl-(p-chlorophenyl-[1-isopropylimidazolyl-(2)]-carbinol.

19. A pharmaceutical preparation as claimed in claim 12, wherein the imidazolyl-(2)-carbinol is [1-benzylimidazolyl-(2)]-[1-methylbenzimidazolyl-(2)]-carbinol.

20. A pharmaceutical preparation as claimed in claim 12, wherein the imidazolyl-(2)-carbinol is 1-[p-(1,1,2-trifluoro-2-chloroethoxy)-phenyl]-1-[1-benzylimidazolyl-(2)]-ethanol.

21. A pharmaceutical composition useful in lowering the serum lipid level in the treatment of hyperlipidemia consisting essentially of a pharmaceutically acceptable carrier and from 100 to 1000 mg per dosage unit of a compound of the formula

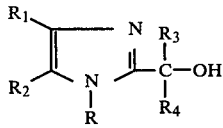

wherein
R is lower alkyl of one to four carbons, phenyl or benzyl,
$R_1$ and $R_2$ are hydrogen,
$R_3$ is lower alkyl or phenyl and
$R_4$ is monohalophenyl or dihalophenyl or of a physiologically tolerable acid addition salt thereof.

22. A method for lowering the serum lipid level in the treatment of hyperlipidemia which comprises administering an effective amount of from 100 to 1000 mg per dosage unit of a compound of the formula I(a)

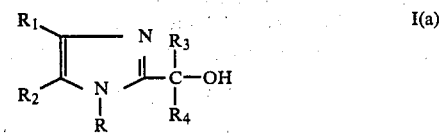

wherein
R = lower alkyl, phenyl or benzyl,
$R_1$ and $R_2$ = hydrogen,
$R_3$ = hydrogen, lower alkyl or phenyl,
$R_4$ = lower haloalkyl, lower haloalkoxyphenyl, 1-benzylimidazol-2-yl, monohalophenyl, dihalophenyl or $R_3$ and $R_4$ are together fluoryl of the formula

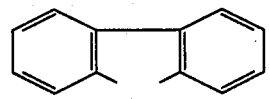

all of said alkyl and alkoxy groups having 1 to 4 carbon atoms, or of a physiologically tolerable acid addition salt thereof.

23. A method for lowering the serum lipid level in the treatment of hyperlipidemia which comprises administering an effective amount of from 100 to 1000 mg per dosage unit of a compound of the formula

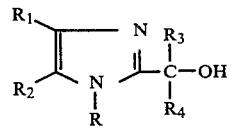

wherein
R is lower alkyl of one to four carbons, phenyl or benzyl,
$R_1$ and $R_2$ are hydrogen,
$R_3$ is lower alkyl or phenyl and
$R_4$ is monohalophenyl or dihalophenyl or of a physiologically tolerable acid addition salt thereof.

24. A method as claimed in claim 23, wherein the imidazolyl-(2)-carbinol is phenyl-(2,4-dichlorophenyl)-[1-methylimidazolyl-(2)]-carbinol or a physiologically tolerable acid addition salt thereof.

25. A method as claimed in claim 23, wherein the imidazolyl-(2)-carbinol is phenyl-(2,4-dichlorophenyl)-[1-methylbenzimidazolyl-(2)]-carbinol or a physiologically tolerable acid addition salt thereof.

* * * * *